United States Patent
Sanders

(10) Patent No.: US 7,583,995 B2
(45) Date of Patent: Sep. 1, 2009

(54) TEMPORARY DISABLEMENT FEATURE FOR IMPLANTABLE DEVICE WITH ANTI-TACHYARRHYTHMIA FUNCTIONS

(75) Inventor: Richard S. Sanders, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 868 days.

(21) Appl. No.: 10/697,999

(22) Filed: Oct. 30, 2003

(65) Prior Publication Data

US 2005/0096703 A1    May 5, 2005

(51) Int. Cl.
*A61N 1/00* (2006.01)
(52) U.S. Cl. ............................ 607/14; 607/9
(58) Field of Classification Search .............. 607/30, 607/31, 32, 60, 9, 4, 5, 16, 17
See application file for complete search history.

(56) References Cited

U.S. PATENT DOCUMENTS

| | | | | |
|---|---|---|---|---|
| 4,236,522 A | * | 12/1980 | McDonald et al. | 607/30 |
| 5,370,666 A | * | 12/1994 | Lindberg et al. | 607/16 |
| 5,385,574 A | * | 1/1995 | Hauser et al. | 607/4 |
| 6,263,246 B1 | * | 7/2001 | Goedeke et al. | 607/60 |
| 6,895,273 B2 | * | 5/2005 | Seim et al. | 607/14 |
| 6,985,773 B2 | * | 1/2006 | Von Arx et al. | 607/32 |

\* cited by examiner

*Primary Examiner*—Carl H Layno
*Assistant Examiner*—Brian T Gedeon
(74) *Attorney, Agent, or Firm*—Schwegman, Lundberg & Woessner, P.A.

(57) ABSTRACT

An implantable cardiac rhythm management device for delivering anti-tachyarrhythmia therapy is provided with a temporary disablement feature so that the delivery of anti-tachyarrhythmia therapy may be conveniently disabled and re-enabled. The feature is particularly useful to patients who are undergoing imaging procedures or surgical procedures where electro-cauterizing instruments may cause inadvertent triggering of cardioversion/defibrillation shocks and/or anti-tachycardia pacing.

20 Claims, 3 Drawing Sheets

TEMPORARY DISABLEMENT FEATURE FOR IMPLANTABLE DEVICE WITH ANTI-TACHYARRHYTHMIA FUNCTIONS

FIELD OF THE INVENTION

This invention pertains to methods and apparatus for treating arrhythmias with electrical therapy.

BACKGROUND

Tachyarrhythmias are abnormal heart rhythms characterized by a rapid rate, typically expressed in units of beats per minute (bpm), that can originate in either the ventricles or the atria. Examples of tachyarrhythmias include atrial tachyarrhythmias such as atrial flutter and atrial fibrillation (AF), and ventricular tachyarrhythmias such as ventricular tachycardia (VT), and ventricular fibrillation (VT). The most dangerous tachyarrhythmias are those that have their origin in the ventricles, namely ventricular tachycardia and ventricular fibrillation. Ventricular rhythms occur when re-entry of a depolarizing wavefront in areas of the ventricular myocardium with different conduction characteristics becomes self-sustaining or when an excitatory focus in the ventricle usurps control of the heart rate from the normal physiological pacemaker of the heart, the sino-atrial node. The result is rapid contraction of the ventricles out of electromechanical synchrony with the atria. Most ventricular rhythms exhibit an abnormal QRS complex in an electrocardiogram (ECG) because they do not use the specialized conduction system of the ventricles, the depolarization spreading instead from the excitatory focus or point of re-entry directly into the myocardium. In ventricular tachycardia, the ventricles contract rapidly and produce distorted QRS complexes in an ECG. Ventricular fibrillation, on the other hand, occurs when the ventricles depolarize at an even more rapid rate and in a chaotic fashion, resulting in QRS complexes of constantly changing shape and virtually no effective pumping action.

Implantable cardiac rhythm management devices may be configured to treat both atrial and ventricular tachyarrhythmias with electrical therapy. Devices known as implantable cardioverter/defibrillators (ICDs) deliver an electric shock to the heart which terminates the tachyarrhythmia by depolarizing all of the myocardium simultaneously and rendering it refractory. The most dangerous tachyarrhythmias are ventricular tachycardia and ventricular fibrillation, and ICDs have most commonly been applied in the treatment of those conditions. Both ventricular tachycardia and ventricular fibrillation are hemodynamically compromising, and both can be life-threatening. Ventricular fibrillation, however, causes circulatory arrest within seconds, is the most common cause of sudden cardiac death, and is usually treated with immediate delivery of a defibrillation shock. Ventricular tachycardia can be treated with either a defibrillation or a cardioversion shock, the latter referring to a shock delivered synchronously with an R wave. Another type of electrical therapy for ventricular tachycardia is antitachycardia pacing (ATP). In ATP, the ventricles are competitively paced with one or more pacing pulses in an effort to interrupt the reentrant circuit causing the tachycardia. ATP therapy can successfully treat VT, but it is not effective in terminating VF. Modern ICDs incorporate ATP capability so that ATP therapy can be delivered to the heart when a ventricular tachycardia is detected. Although cardioversion/defibrillation will also terminate ventricular tachycardia, it consumes a large amount of stored power from the battery and results in patient discomfort owing to the high voltage of the shock pulses. It is desirable, therefore, for the ICD to use ATP to terminate a tachyarrhythmia whenever possible. In most ICDs with ATP capability, VF is distinguished from VT using a rate-based criterion so that ATP or shock therapy can be delivered as appropriate, where the heart rate is determined by measurement of the time interval between successive ventricular depolarizations. In a typical device, a tachyarrhythmia with a heart rate in the VT zone is treated with ATP therapy in order to avoid an unnecessary painful shock to the patient, and a defibrillation shock is delivered if the heart rate is in the VF zone or if ATP pacing fails to terminate a tachyarrhythmia in the VT zone.

ICDs are also capable of detecting atrial tachyarrhythmias, such as atrial fibrillation and atrial flutter, and delivering a cardioversion shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

As noted above, ICDs detect tachyarrhythmias by measuring the time intervals between successive depolarizations of the atria or ventricles. Situations arise, however, where such devices are subjected to externally produced oscillating electromagnetic fields, referred to as electromagnetic interference or EMI, which are sensed by sensing electrodes and falsely interpreted as cardiac depolarizations. If the frequency at which the externally produced field oscillates is within a range similar to that of a tachyarrhythmia, inadvertent triggering of anti-tachyarrhythmia therapy, such as anti-tachycardia pacing or delivery of a cardioversion/defibrillation shock, can occur. One example of such a situation is during a surgical operation where the electro-cauterizing instruments used to control bleeding can produce EMI that triggers the delivery of anti-tachyarrhythmia therapy by the device. It is therefore common practice to de-activate such anti-tachyarrhythmia functions in ICDs when the patient is expected to be exposed to such electromagnetic interference. De-activating a device before a surgical operation, imaging procedure, or other event and then re-activating it afterwards, however, requires the use of an external programmer in both instances and can be inconvenient. It may even pose a risk to the patient if the re-activation is not done promptly. The present invention is directed toward an improved method and device for dealing with this problem.

SUMMARY

In accordance with the present invention, an implantable cardiac rhythm management device for delivering anti-tachyarrhythmia therapy in the form of cardioversion/defibrillation shocks and/or anti-tachycardia pacing is configured so that anti-tachyarrhythmia therapy may be temporarily disabled by a command via a wireless telemetry link from an external device such as an external programmer. In one embodiment, anti-tachyarrhythmia therapy is re-enabled after expiration of a specified time interval which may be either a fixed value or specified by the external device. In other embodiments, anti-tachyarrhythmia therapy is re-enabled by actuation of a magnetic switch or when the implantable device measures an activity level above a specified threshold value.

DETAILED DESCRIPTION

The present invention may be embodied by an implantable cardiac rhythm management device for delivering anti-tachyarrhythmia therapy through one or more electrical stimulation channels which is configured for temporary disablement of the anti-tachyarrhythmia therapy when the need arises. Below is a description of an exemplary hardware platform followed by a detailed description of different techniques for implementing the temporary disablement feature.

1. Exemplary Device Description

Figure 1:
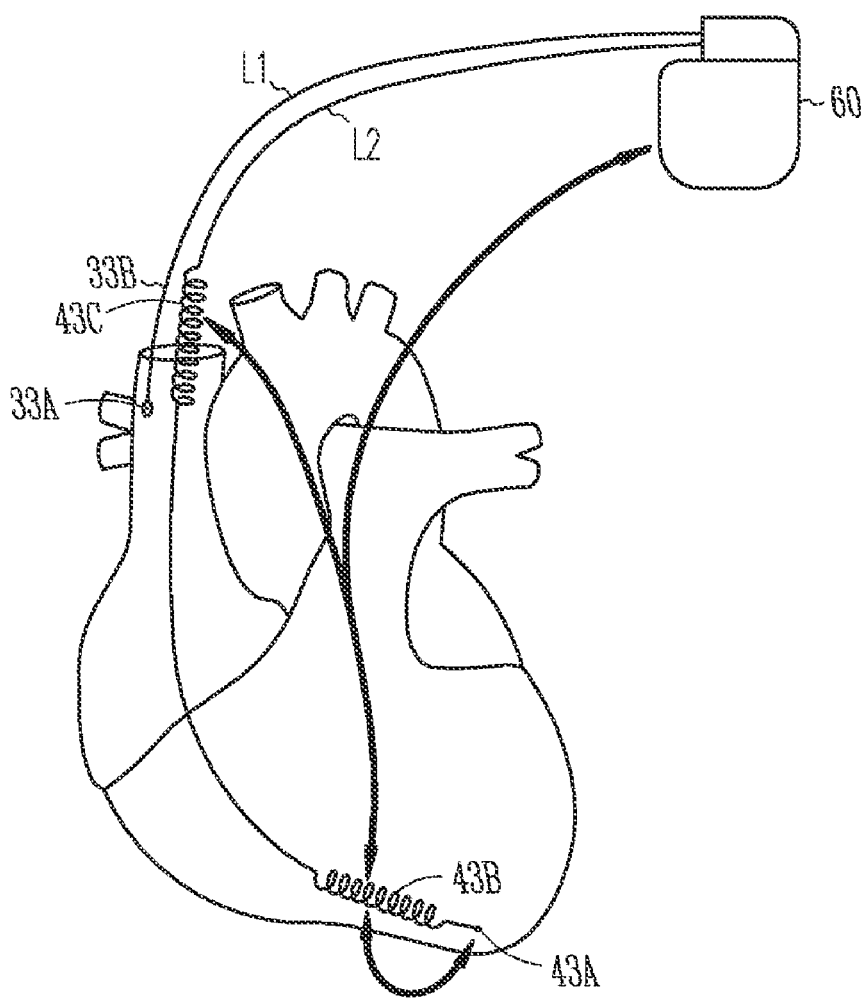
FIG. 1 depicts an exemplary physical configuration of an implanted cardiac rhythm management device.

Cardiac rhythm management devices such as ICDs and pacemakers are typically implanted subcutaneously on a patient's chest and have leads threaded intravenously into the heart to connect the device to electrodes used for sensing cardiac activity, delivering pacing pulses, and/or delivering defibrillation shocks. FIG. 1 depicts an implantable cardioverter/defibrillator device for treating atrial and ventricular tachyarrhythmias that also incorporates functionality for pacing the atria and/or the ventricles in a bradycardia pacing mode. The device includes a subcutaneously implantable housing or can 60 for enclosing the electronic circuitry of the device and a pair of leads L1 and L2 having electrodes incorporated therein. The lead L1 has a tip electrode 33*a* and ring electrode 33*b* which are shown in the figure as disposed in the superior vena cava (SVC) for pacing or sensing of the atria. The lead L2 has a tip electrode 43*a*, a distal coil electrode 43*b*, and a proximal coil electrode 43*c*. Coil electrodes can be used to deliver pacing pulses but are designed especially for delivering cardioversion/defibrillation shocks. In the placement of the lead L2 shown in the figure, tip electrode 43*a* and distal coil electrode 43*b* are disposed in the right ventricle (RV), and proximal coil electrode 43*c* is disposed in the superior vena cava or right atrium. Sensing or pacing of the ventricles may be performed using tip electrode 43*a* and/or coil electrode 43*b*. A ventricular cardioversion/defibrillation shock may be delivered between coil 43*b* and the can 60, or between coil 43*b* and the can 60 electrically in common with the coil 43*c*, and an atrial cardioversion shock may be delivered between the coil 43*c* and the can 60.

Figure 2:
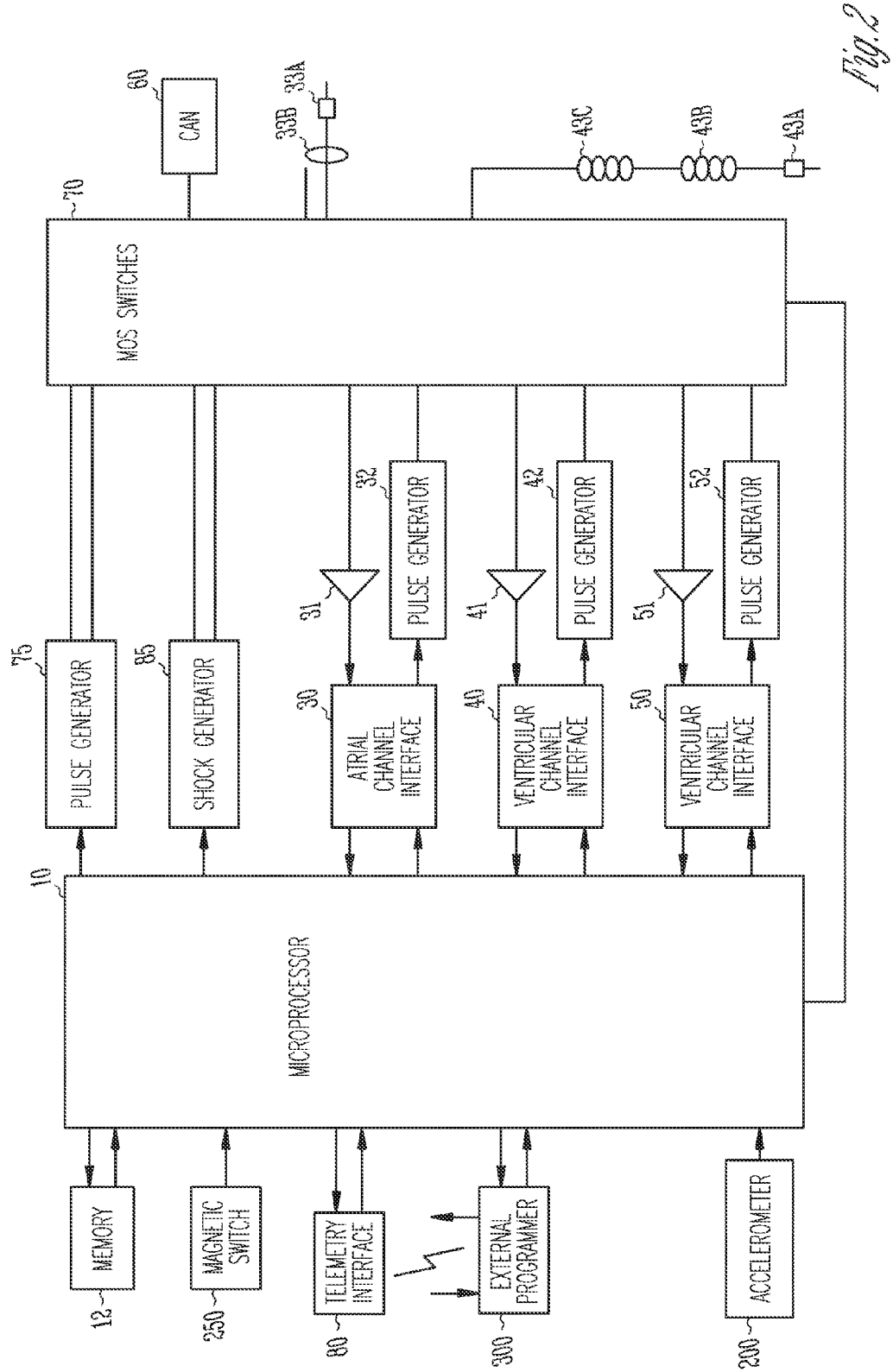
FIG. 2 is a system diagram of an implantable cardiac rhythm management device.

FIG. 2 is a system diagram the implantable device shown in FIG. 1. The controller of the device is made up of a microprocessor 10 communicating with a memory 12, where the memory 12 may comprise a ROM (read-only memory) for program storage and a RAM (random-access memory) for data storage. A microprocessor-type controller 10 controls the overall operation of the device in accordance with programmed instructions stored in memory. The controller could be implemented by other types of logic circuitry (e.g., discrete components or programmable logic arrays) using a state machine type of design, but a microprocessor-based system is preferable. As used herein, the terms "circuitry" and "controller" should be taken to refer to either discrete logic circuitry or to the programming of a microprocessor. A telemetry interface 80 is provided by which the controller may wirelessly communicate with an external programmer 300. The external programmer 300 is a computerized device that can interrogate the implantable device and receive stored data as well as adjust the device's operating parameters.

The device is equipped with multiple sensing amplifiers and pulse generators which can be configured as channels for pacing and/or sensing selected heart chambers. A MOS switch matrix 70 controlled by the microprocessor is used to configure a sensing or pacing channel by switching selected electrodes to the input of a sense amplifier or to the output of a pulse generator. The switch matrix 70 allows the device to employ either bipolar sensing/pacing using two closely spaced electrodes of a lead or unipolar sensing/pacing using one of the electrodes of a lead and the can 60 as a reference electrode. The switch matrix 70 can also connect atrial shock generator 75 to deliver an atrial cardioversion shock between coil electrode 43*c* and the can 60, and can connect ventricular shock generator 85 to deliver a ventricular cardioversion/defibrillation shock between coil electrode 43*b* and the can 60 (or the can 60 connected in common with the coil electrode 43*c*). In the device shown in FIG. 2, an atrial channel for sensing or pacing an atrial site is configured with tip electrode 33*a*, ring electrode 33*b*, sense amplifier 31, pulse generator 32, and an atrial channel interface 30 which communicates bidirectionally with a port of microprocessor 10. A first ventricular channel for sensing or pacing a ventricular site is configured with tip electrode 43*a*, coil electrode 43*b*, sense amplifier 41, pulse generator 42, and ventricular channel interface 40. A second ventricular channel for sensing or pacing a ventricular site is configured with tip electrode 43*a*, coil electrode 43*b*, sense amplifier 51, pulse generator 52, and ventricular channel interface 50. A second ventricular sensing channel using ventricular channel interface 50 may be configured by connecting one of the differential inputs of sense amplifier 51 to the coil electrode 43*b* and connecting the other input to the can 60 and coil electrode 43*c*.

The channel interfaces may include comparators for comparing received electrogram signals to reference values, analog-to-digital converters for digitizing sensing signal inputs from the sensing amplifiers, registers that can be written to for adjusting the gain and sensing threshold values of the sensing amplifiers, and registers for controlling the output of pacing pulses and/or adjusting the pacing pulse energy by changing the pulse amplitude or pulse width. The controller uses the sensing channels in order to detect intrinsic cardiac activity in a heart chamber, referred to as a chamber sense (e.g., an atrial sense or a ventricular sense). In order to detect intrinsic cardiac activity, the signals emanating from the sense amplifier are compared with a reference potential. As described above, a sensing channel includes sense amplifier circuits for amplifying and filtering the electrogram signals picked up by an electrode disposed at a cardiac site. Only when an electrogram signal from the sense amplifier exceeds a reference potential, referred to as a sensing threshold, is it treated as a chamber sense. The sensing threshold may be implemented with analog circuitry, where the sense amplifier output is applied to one input of a comparator circuit whose other input is connected to a reference potential, or with digital circuitry operating on digitized samples of the sense amplifier output which are compared with a digitized reference value. In either case, the sensing threshold for each channel is adjustable by the controller. Detected chamber senses may be used for controlling the delivery of paces in accordance with a programmed pacing mode (e.g., bradycardia pacing or ventricular anti-tachycardia pacing) and/or for diagnostic purposes.

By counting the number of chamber senses over a defined time period or measuring the time intervals between senses, the controller is able to measure heart rate and detect arrhythmias using rate-based criteria. The atrial and ventricular sensing channels described above are used to separately measure the atrial and ventricular rates in this embodiment.

When the measured atrial and/or ventricular rates exceed specified threshold values, the device detects a tachyarrhythmia and is programmed to respond with appropriate anti-tachyarrhythmia therapy. For example, if a ventricular rate is measured which is in the VF zone, the device delivers a ventricular defibrillation shock. If a ventricular rate is measured which is in the VT zone, the device decides whether VT or an atrial tachyarrhythmia is present using rate and/or electrogram morphology criteria. If the ventricular rate is greater than the atrial rate, VT is detected, and the device may be programmed to initiate ventricular anti-tachycardia pacing. If the atrial rate is greater than or equal to the ventricular rate and a specified minimum number of normally conducted beats are detected, an atrial tachyarrhythmia is detected, the device is programmed to deliver an atrial cardioversion shock. The device would also detect an atrial tachyarrhythmia and deliver an atrial cardioversion shock if the atrial rate is above a specified threshold value and the ventricular rate is in the normal range, as could occur in a patient without an intact AV conduction pathway. To lessen the risk of inducing a ventricular arrhythmia, the device may deliver the atrial cardioversion shock synchronously with a sensed ventricular depolarization (i.e., an R wave) and may delay delivering the shock until the intrinsic ventricular rhythm is below a specified maximum rate.

2. Temporary Disablement of Anti-Tachyarrhythmia Therapy

As described above, certain medical and surgical procedures involve the use of instrumentation capable of producing electromagnetic interference which can trigger the delivery of anti-tachyarrhythmia therapy by an implantable device. Such a device would typically include, as illustrated in FIG. 2, a sensing channel for sensing an electrogram signal representing cardiac electrical activity and circuitry for generating a chamber sense when the electrogram signal exceeds a specified threshold, one or more stimulation channels for delivering electrical stimulation to a subject's heart, a controller programmed to detect a tachyarrhythmia from the rate at which chamber senses are generated and to cause delivery of ant-tachyarrhythmia therapy through one or more of the stimulation channels upon detection of a tachyarrhythmia, and a telemetry interface by which the controller may communicate with an external device. The one or more stimulation channels may include a pacing channel for delivering pacing therapy (eg., anti-tachycardia pacing or bradycardia pacing) and/or a shock channel for delivering cardioversion/defibrillation shocks, where the controller is programmed to cause delivery of anti-tachyarrhythmia therapy in the form of anti-tachycardia pacing and/or a cardioversion/defibrillation shock upon detection of a tachyarrhythmia. If the device is capable of delivering anti-tachycardia pacing and cardioversion/defibrillation shocks, the controller is programmed to deliver anti-tachycardia pacing upon detection of a tachyarrhythmia in a tachycardia zone and deliver a cardioversion/defibrillation shock upon detection of a tachyarrhythmia in a fibrillation zone. In accordance with the invention, the device is configured by appropriate programming of the controller to disable the delivery of anti-tachyarrhythmia therapy for a specified time interval upon receipt of a temporary suspend command from the external device via the telemetry interface and to re-enable the delivery of anti-tachyarrhythmia therapy upon expiration of the specified time interval. The specified time interval for which the delivery of anti-tachyarrhythmia therapy is disabled may be a fixed interval or a variable interval communicated to the implantable device by the external device via the telemetry link.

Disablement of anti-tachyarrhythmia therapy may be accomplished in different ways. In one embodiment, the device continues to sense cardiac activity but is prevented from delivering anti-tachyarrhythmia therapy if a tachyarrhythmia is detected while the disablement feature is active. In another embodiment, disablement of anti-tachyarrhythmia therapy is effected by disabling the device's sensing channels. A sensing channel may be disabled directly or indirectly such as by raising its sensing threshold to render it refractory. Raising the sensing threshold of a sensing channel to its maximum value (e.g., infinity) means that no cardiac activity, and hence no tachyarrhythmias, will be detected, and the device will therefore be disabled from delivering anti-tachyarrhythmia therapy.

Disabling anti-tachyarrhythmia therapy by disabling the sensing functions of a device may also be advantageous in the case where the device is also delivering bradycardia pacing therapy to the patient. Bradycardia pacing modes refer to pacing algorithms used to pace the atria and/or ventricles in a manner that enforces a certain minimum heart rate. Because of the risk of inducing an arrhythmia with asynchronous pacing, most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. In an environment where electromagnetic interference is present, a device operating in an inhibited demand pacing mode may interpret the electromagnetic interference as intrinsic beats which then inhibit the delivery of paces. Some patients are not able to tolerate the complete cessation of pacing therapy, however. Disabling the sensing channels of the device deals with this problem by preventing the device from detecting cardiac activity. The device then delivers paces at the programmed lower rate limit, thus essentially reverting to an asynchronous pacing mode during the time the sensing channels are disabled.

Figure 3:
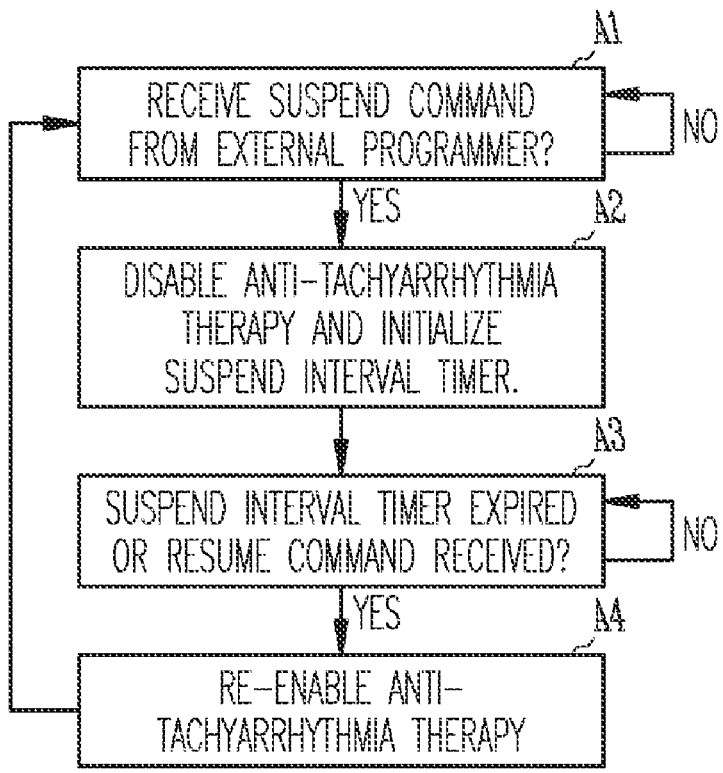
FIG. 3 illustrates an exemplary algorithm for implementing the present invention.

FIG. 3 illustrates an exemplary algorithm for implementing this feature as it would be executed by the controller. At step A1, the device waits for a temporary suspend command from an external programmer via the telemetry interface. Upon receipt of such a command and a specified suspend interval from the external programmer, the device disables anti-tachyarrhythmia therapy and initializes a timer (e.g., a timer implemented in code executed by the controller) to the specified suspend interval at step A2. At step A3, the device waits for expiration of the suspend interval or receipt of a resume command from the external programmer. Upon occurrence of either of these events, the device re-enables anti-tachyarrhythmia therapy at step A4 and returns to step A1. In other embodiments, the implantable device further includes a magnetic switch actuated by application of a magnetic field (illustrated as switch 250 in FIG. 2) so that delivery of anti-tachyarrhythmia therapy is re-enabled before expiration of the specified suspend interval by actuation of the magnetic switch and/or an activity sensor for measuring an activity level (illustrated as accelerometer 200 in FIG. 2) so that delivery of anti-tachyarrhythmia therapy is re-enabled before expiration of the specified suspend interval upon measurement of an activity level above a specified threshold value.

It may be desirable in certain circumstances, of course, to indefinitely disable anti-tachyarrhythmia therapy in an implantable device. Therefore, the controller may be programmed to disable the delivery of anti-tachyarrhythmia therapy indefinitely upon receipt of an indefinite suspend command from the external programmer via the telemetry interface and to re-enable the delivery of anti-tachyarrhythmia therapy upon receipt of a resume command. In order to eliminate the need for an external programmer in order to re-enable anti-tachyarrhythmia therapy, the implantable device may further include a magnetic switch actuated by application of a magnetic field so that the resume command is communicated to the implantable device by actuation of the magnetic switch and/or an activity sensor for measuring an activity level so that the resume command is generated upon measurement of an activity level above a specified threshold value.

As described above, disablement of anti-tachyarrhythmia therapy may be effected in one embodiment by disabling the sensing functions of the device. It should be appreciated that a temporary sensing channel disablement feature may be incorporated into a bradycardia pacemaker without the capability of delivering anti-tachyarrhythmia therapy. Disabling the sensing channels of such a device causes it to revert to an asynchronous pacing mode which may be desirable in situations where electromagnetic interference is expected to be present. Disabling and re-enabling the sensing channels of the device may be accomplished in different embodiments by any of the techniques for disabling and re-enabling anti-tachyarrhythmia therapy described above.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. An implantable cardiac rhythm management device, comprising:
    a sensing channel for sensing an electrogram signal representing cardiac electrical activity and circuitry for generating a chamber sense when the electrogram signal exceeds a specified threshold;
    one or more stimulation channels for delivering electrical stimulation to a subject's heart;
    an activity sensor for measuring an activity level;
    a controller programmed to detect a tachyarrhythmia from the rate at which chamber senses are generated and to cause delivery of anti-tachyarrhythmia therapy through one or more of the stimulation channels upon detection of a tachyarrhythmia;
    a telemetry interface by which the controller may communicate with an external device;
    wherein the controller is programmed to disable the delivery of anti-tachyarrhythmia therapy for a specified time interval upon receipt of a temporary suspend command from the external device via the telemetry interface and to re-enable the delivery of anti-tachyarrhythmia therapy upon expiration of the specified time interval; and,
    wherein the controller is programmed to re-enable delivery of anti-tachyarrhythmia therapy before expiration of the specified time interval upon measurement of an activity level above a specified threshold value.

2. The device of claim 1 wherein the specified time interval for which the delivery of anti-tachyarrhythmia therapy is disabled is communicated to the implantable device by the external device via the telemetry interface.

3. The device of claim 1 wherein delivery of anti-tachyarrhythmia therapy is re-enabled before expiration of the specified time interval by receipt of a resume command from the external device via the telemetry interface.

4. The device of claim 1 further comprising a magnetic switch actuated by application of a magnetic field and wherein delivery of anti-tachyarrhythmia therapy is re-enabled before expiration of the specified time interval by actuation of the magnetic switch.

5. The device of claim 1 wherein the controller is further programmed to disable the delivery of anti-tachyarrhythmia therapy indefinitely upon receipt of an indefinite suspend command from the external device via the telemetry interface and to re-enable the delivery of anti-tachyarrhythmia therapy upon receipt of a resume command.

6. The device of claim 5 further comprising a magnetic switch actuated by application of a magnetic field and wherein the resume command is communicated to the implantable device by actuation of the magnetic switch.

7. The device of claim 5 wherein the resume command is generated upon measurement of an activity level above a specified threshold value.

8. The device of claim 1 further comprising a magnetic switch actuated by application of a magnetic field and wherein the controller is further programmed to disable the delivery of anti-tachyarrhythmia therapy indefinitely upon receipt of an indefinite suspend with magnetic re-enable command from the external device and to re-enable the delivery of anti-tachyarrhythmia therapy upon actuation of the magnetic switch.

9. The device of claim 1 wherein the one or more stimulation channels include a pacing channel for delivering anti-tachycardia pacing and wherein the controller is programmed to cause delivery of anti-tachyarrhythmia therapy in the form of anti-tachycardia pacing upon detection of a tachyarrhythmia.

10. The device of claim 1 wherein the one or more stimulation channels include a shock channel for delivering cardioversion/defibrillation shocks and wherein the controller is programmed to cause delivery of anti-tachyarrhythmia therapy in the form of a cardioversion/defibrillation shock upon detection of a tachyarrhythmia.

11. The device of claim 1 wherein the one or more stimulation channels include a pacing channel for delivering anti-tachycardia pacing and a shock channel for delivering cardioversion/defibrillation shocks, and wherein the controller is programmed to cause delivery of anti-tachyarrhythmia therapy in the form of anti-tachycardia pacing upon detection of a tachyarrhythmia in a tachycardia zone and in the form of a cardioversion/defibrillation shock upon detection of a tachyarrhythmia in a fibrillation zone.

12. The device of claim 1 wherein the controller is programmed to disable anti-tachyarrhythmia therapy by disabling one or more sensing channels.

13. The device of claim 1 wherein the one or more stimulation channels include a pacing channel for delivering bradycardia pacing in an inhibited demand mode and further wherein the controller is programmed to disable anti-tachyarrhythmia therapy by disabling one or more sensing channels which thereby also causes the device to revert to an asynchronous pacing mode.

14. An implantable cardiac rhythm management device, comprising:

a sensing channel for sensing an electrogram signal representing cardiac electrical activity and circuitry for generating a chamber sense when the electrogram signal exceeds a specified threshold;

one or more stimulation channels for delivering electrical stimulation to a subject's heart;

a controller programmed to detect a tachyarrhythmia from the rate at which chamber senses are generated and to cause delivery of anti-tachyarrhythmia therapy through one or more of the stimulation channels upon detection of a tachyarrhythmia;

a magnetic switch interfaced to the controller which is actuated by application of a magnetic field;

a telemetry interface by which the controller may communicate with an external device; and, wherein the controller is programmed to disable the delivery of anti-tachyarrhythmia therapy indefinitely upon receipt of an indefinite suspend with magnetic re-enable command from the external device and to re-enable the delivery of anti-tachyarrhythmia therapy upon actuation of the magnetic switch.

15. The device of claim 14 wherein the controller is programmed to disable the delivery of anti-tachyarrhythmia therapy for a specified time interval upon receipt of a temporary suspend command from the external device via the telemetry interface and to re-enable the delivery of anti-tachyarrhythmia therapy upon expiration of the specified time interval.

16. The device of claim 15 wherein the controller is programmed to re-enable delivery of anti-tachyarrhythmia therapy before expiration of the specified time interval by actuation of the magnetic switch.

17. The device of claim 14 wherein the one or more stimulation channels include a pacing channel for delivering bradycardia pacing in an inhibited demand mode and further wherein the controller is programmed to disable anti-tachyarrhythmia therapy by disabling the sensing channel which thereby also causes the device to revert to an asynchronous pacing mode.

18. An implantable cardiac rhythm management device, comprising:

a sensing channel for sensing an electrogram signal representing cardiac electrical activity and circuitry for generating a chamber sense when the electrogram signal exceeds a specified threshold;

one or more stimulation channels for delivering electrical stimulation to a subject's heart;

a controller programmed to detect a tachyarrhythmia from the rate at which chamber senses are generated and to cause delivery of anti-tachyarrhythmia therapy through one or more of the stimulation channels upon detection of a tachyarrhythmia;

an activity sensor interfaced to the controller for measuring an activity level;

a telemetry interface by which the controller may communicate with an external device; and, wherein the controller is programmed to disable the delivery of the anti-tachyarrhythmia therapy indefinitely upon receipt of an indefinite suspend with activity re-enable command from the external device and to re-enable the delivery of anti-tachyarrhythmia therapy upon measurement of an activity level above a specified threshold value.

19. The device of claim 18 wherein the one or more stimulation channels include a pacing channel for delivering bradycardia pacing in an inhibited demand mode and further wherein the controller is programmed to disable anti-tachyarrhythmia therapy by disabling the sensing channel which thereby also causes the device to revert to an asynchronous pacing mode.

20. The device of claim 18 further comprising a magnetic switch interfaced to the controller which is actuated by application of a magnetic field and wherein the controller is programmed to re-enable delivery of anti-tachyarrhythmia therapy by actuation of the magnetic switch.

* * * * *

UNITED STATES PATENT AND TRADEMARK OFFICE
CERTIFICATE OF CORRECTION

PATENT NO.        : 7,583,995 B2                                          Page 1 of 1
APPLICATION NO.   : 10/697999
DATED             : September 1, 2009
INVENTOR(S)       : Richard S. Sanders It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1356 days.

Signed and Sealed this

Fourteenth Day of September, 2010

David J. Kappos
*Director of the United States Patent and Trademark Office*